United States Patent [19]
Glaug et al.

[11] Patent Number: 5,601,544
[45] Date of Patent: Feb. 11, 1997

[54] CHILD'S TRAINING PANT WITH ELASTICIZED SHAPED ABSORBENT AND METHOD OF MAKING THE SAME

[75] Inventors: Frank S. Glaug; Richard H. Thiessen, both of Appleton; Robert L. Popp, Hortonville; Shirlee A. Weber, Neenah; Richard T. Wehrle, New London, all of Wis.

[73] Assignee: Kimberly-Clark Corporation, Neenah, Wis.

[21] Appl. No.: 171,580

[22] Filed: Dec. 23, 1993

[51] Int. Cl.⁶ .................................................. A61F 13/15
[52] U.S. Cl. ...................... 604/385.2; 604/393; 604/396; 604/373
[58] Field of Search ............................... 604/373, 385.1, 604/385.2, 393–396

[56] References Cited

U.S. PATENT DOCUMENTS

| | | |
|---|---|---|
| Re. 26,151 | 1/1967 | Duncan et al. . |
| Re. 28,483 | 7/1975 | Ralph . |
| Re. 30,057 | 7/1979 | Schaar . |
| Re. 33,106 | 11/1989 | Beckestrom .......................... 604/385.2 |
| 50,308 | 10/1865 | Ware . |
| 188,940 | 3/1877 | Packscher . |
| 1,001,940 | 8/1911 | Epstein . |
| 1,201,860 | 10/1916 | Nelke . |
| 1,419,044 | 6/1922 | Gunderson . |
| 1,508,740 | 9/1924 | Brand . |
| 1,655,300 | 1/1928 | Vizzard . |
| 1,971,671 | 8/1934 | Alsop . |
| 1,977,604 | 10/1934 | Alsop . |
| 2,004,088 | 6/1935 | Alsop . |
| 2,026,158 | 12/1935 | Bennett . |
| 2,052,598 | 9/1936 | Berg ........................................ 128/288 |
| 2,078,512 | 4/1937 | Simpson . |
| 2,102,359 | 12/1937 | Frieman . |
| 2,141,105 | 12/1938 | Eller et al. . |
| 2,166,012 | 7/1939 | Maida . |

(List continued on next page.)

FOREIGN PATENT DOCUMENTS

| | | |
|---|---|---|
| 86044/82 | 1/1983 | Australia . |
| 21332/83 | 5/1984 | Australia . |
| 45217/85 | 2/1986 | Australia . |
| 188667 | 4/1956 | Austria . |
| 1175602 | 10/1984 | Canada . |
| 1211902 | 9/1986 | Canada . |
| 1216702 | 1/1987 | Canada . |
| 1238151 | 6/1988 | Canada . |
| 1302654 | 6/1992 | Canada . |
| 0070584A1 | 1/1983 | European Pat. Off. . |
| 0098512A2 | 1/1984 | European Pat. Off. . |
| 0109126A1 | 5/1984 | European Pat. Off. . |
| 0149999A2 | 7/1985 | European Pat. Off. . |
| 0183668A2 | 6/1986 | European Pat. Off. . |
| 0190881A2 | 8/1986 | European Pat. Off. . |
| 0203712A1 | 12/1986 | European Pat. Off. . |
| 0219326A2 | 4/1987 | European Pat. Off. . |
| 0091412B2 | 5/1987 | European Pat. Off. . |
| 0243013A1 | 10/1987 | European Pat. Off. . |
| 0130848B1 | 11/1987 | European Pat. Off. . |
| 0251332A2 | 1/1988 | European Pat. Off. . |
| 0264952A2 | 4/1988 | European Pat. Off. . |
| 0264238A1 | 4/1988 | European Pat. Off. . |
| 0268858A2 | 6/1988 | European Pat. Off. . |
| 0134086B1 | 1/1989 | European Pat. Off. . |
| 0304631A1 | 3/1989 | European Pat. Off. . |
| 0309246A1 | 3/1989 | European Pat. Off. . |
| 0311333A2 | 4/1989 | European Pat. Off. . |
| 0324133A1 | 7/1989 | European Pat. Off. . |
| 0323634A3 | 7/1989 | European Pat. Off. . |

(List continued on next page.)

Primary Examiner—Robert A. H. Clarke
Attorney, Agent, or Firm—Douglas L. Miller

[57] ABSTRACT

A child's training pant includes a pant body having a waist opening and a pair of leg openings, and an elasticized shaped absorbent composite having elasticized absorbent side portions. Elasticized side flaps are formed from a liquid impermeable material situated between the absorbent composite and the pant body. A method is also provided for making a training pant.

19 Claims, 7 Drawing Sheets

U.S. PATENT DOCUMENTS

| | | |
|---|---|---|
| 2,201,255 | 5/1940 | Wilson, Jr. . |
| 2,252,019 | 8/1941 | Meinecke et al. . |
| 2,252,992 | 8/1941 | Steiner . |
| 2,261,810 | 11/1941 | Reiner . |
| 2,266,518 | 12/1941 | Sarge . |
| 2,317,768 | 4/1943 | Holland et al. . |
| 2,397,641 | 4/1946 | Blair . |
| 2,419,867 | 4/1947 | Woodman . |
| 2,435,945 | 2/1948 | Redmond . |
| 2,468,445 | 4/1949 | Hurst . |
| 2,494,261 | 1/1950 | Owenby . |
| 2,509,674 | 5/1950 | Cohen . |
| 2,538,596 | 1/1951 | Sheridan . |
| 2,538,758 | 1/1951 | Bricmont . |
| 2,544,069 | 3/1951 | Cutler . |
| 2,545,674 | 3/1951 | Ralph . |
| 2,575,164 | 11/1951 | Donovan . |
| 2,616,427 | 11/1952 | Pettit . |
| 2,662,526 | 12/1953 | Sanford . |
| 2,675,805 | 4/1954 | Trimble . |
| 2,787,271 | 4/1957 | Clark . |
| 2,827,052 | 3/1958 | Goodman et al. . |
| 2,840,077 | 6/1958 | Morgan . |
| 2,893,393 | 7/1959 | Pressley . |
| 2,895,477 | 7/1959 | Bernard . |
| 2,916,037 | 12/1959 | Hansen . |
| 2,921,583 | 1/1960 | Lerner . |
| 2,951,481 | 9/1960 | Gordon . |
| 2,964,040 | 12/1960 | Ashton et al. . |
| 2,969,065 | 1/1961 | Farnsworth . |
| 3,000,381 | 9/1961 | Mulhole et al. . |
| 3,087,495 | 4/1963 | Hart . |
| 3,098,484 | 7/1963 | Younger . |
| 3,142,301 | 7/1964 | Erteszek . |
| 3,180,335 | 4/1965 | Duncan et al. . |
| 3,182,661 | 5/1965 | Ribeiro et al. . |
| 3,237,625 | 3/1966 | Johnson . |
| 3,349,769 | 10/1967 | Piekarski . |
| 3,364,931 | 1/1968 | Hirsch . |
| 3,368,563 | 2/1968 | Scheier . |
| 3,386,442 | 6/1968 | Sabee . |
| 3,386,446 | 6/1968 | Sloan . |
| 3,397,696 | 8/1968 | Rickard . |
| 3,417,751 | 12/1968 | Murdoch . |
| 3,424,162 | 1/1969 | Parravicini . |
| 3,426,756 | 2/1969 | Romanek . |
| 3,452,753 | 7/1969 | Sanford . |
| 3,461,872 | 8/1969 | McConnell et al. . |
| 3,481,337 | 12/1969 | Ruffo . |
| 3,509,881 | 5/1970 | Sabee . |
| 3,530,859 | 9/1970 | Heimowitz . |
| 3,532,093 | 10/1970 | Lovret . |
| 3,572,342 | 3/1971 | Lindquist et al. . |
| 3,575,174 | 4/1971 | Mogor . |
| 3,592,194 | 7/1971 | Duncan . |
| 3,593,716 | 7/1971 | Vogt . |
| 3,599,640 | 8/1971 | Larson . |
| 3,612,055 | 10/1971 | Mesek et al. . |
| 3,613,687 | 10/1971 | Kennedy . |
| 3,658,063 | 4/1972 | Schaar . |
| 3,658,064 | 4/1972 | Pociluyko . |
| 3,665,920 | 5/1972 | Davis . |
| 3,667,466 | 6/1972 | Ralph . |
| 3,687,141 | 8/1972 | Matsuda . |
| 3,744,494 | 7/1973 | Marsan . |
| 3,765,418 | 10/1973 | Jones, Sr. . |
| 3,768,481 | 10/1973 | Shibata . |
| 3,771,524 | 11/1973 | Ralph . |
| 3,776,233 | 12/1973 | Schaar . |
| 3,779,246 | 12/1973 | Mesek et al. . |
| 3,807,402 | 4/1974 | Miller et al. . |
| 3,825,006 | 7/1974 | Ralph . |
| 3,848,594 | 11/1974 | Buell . |
| 3,860,003 | 1/1975 | Buell . |
| 3,881,488 | 5/1975 | Delanty et al. . |
| 3,884,234 | 5/1975 | Taylor . |
| 3,885,568 | 5/1975 | Schaar . |
| 3,890,973 | 6/1975 | Davis et al. . |
| 3,901,236 | 8/1975 | Assarsson et al. . |
| 3,913,578 | 10/1975 | Schaar . |
| 3,920,017 | 11/1975 | Karami . |
| 3,929,134 | 12/1975 | Karami . |
| 3,930,090 | 12/1975 | Campbell, Sr. et al. . |
| 3,930,501 | 1/1976 | Schaar . |
| 3,930,502 | 1/1976 | Tritsch . |
| 3,943,930 | 3/1976 | Schaar . |
| 3,952,745 | 4/1976 | Duncan . |
| 3,965,906 | 6/1976 | Karami . |
| 3,978,861 | 9/1976 | Schaar . |
| 3,987,794 | 10/1976 | Schaar . |
| 3,995,637 | 12/1976 | Schaar . |
| 3,995,640 | 12/1976 | Schaar . |
| 3,999,547 | 12/1976 | Hernandez . |
| 3,999,548 | 12/1976 | Hernandez . |
| 4,029,100 | 6/1977 | Karami . |
| 4,031,568 | 6/1977 | Huff . |
| 4,040,423 | 8/1977 | Jones, Sr. . |
| 4,041,950 | 8/1977 | Jones, Sr. . |
| 4,044,769 | 8/1977 | Papajohn . |
| 4,050,462 | 9/1977 | Woon et al. . |
| 4,067,068 | 1/1978 | Bregstein et al. . |
| 4,069,822 | 1/1978 | Buell . |
| 4,076,663 | 2/1978 | Masuda et al. . |
| 4,081,301 | 3/1978 | Buell . |
| 4,090,515 | 5/1978 | Karami . |
| 4,100,324 | 7/1978 | Anderson et al. . |
| 4,100,922 | 7/1978 | Hernandez . |
| 4,122,552 | 10/1978 | Tedford . |
| 4,129,132 | 12/1978 | Butterworth et al. . |
| 4,166,464 | 9/1979 | Korpman . |
| 4,182,336 | 1/1980 | Black . |
| 4,187,342 | 2/1980 | Holst et al. . |
| 4,200,102 | 4/1980 | Duhamel et al. . |
| 4,205,679 | 6/1980 | Repke et al. . |
| 4,210,143 | 7/1980 | De Jonckheere . |
| 4,210,144 | 7/1980 | Sarge, III et al. . |
| 4,226,238 | 10/1980 | Bianco . |
| 4,227,531 | 10/1980 | McLeod . |
| 4,227,952 | 10/1980 | Sabee . |
| 4,232,674 | 11/1980 | Melican . |
| 4,239,578 | 12/1980 | Gore . |
| 4,246,900 | 1/1981 | Schroder . |
| 4,253,461 | 3/1981 | Strickland et al. . |
| 4,261,782 | 4/1981 | Teed . |
| 4,285,343 | 8/1981 | McNair . |
| 4,286,082 | 8/1981 | Tsubakimoto et al. . |
| 4,309,236 | 1/1982 | Teed . |
| 4,315,508 | 2/1982 | Bolick . |
| 4,319,572 | 3/1982 | Widlund et al. . |
| 4,323,070 | 4/1982 | Ternstrom et al. . |
| 4,324,245 | 4/1982 | Mesek et al. . |
| 4,325,372 | 4/1982 | Teed . |
| 4,326,528 | 4/1982 | Ryan et al. . |
| 4,333,466 | 6/1982 | Matthews . |
| 4,351,340 | 9/1982 | McLeod . |
| 4,352,355 | 10/1982 | Mesek et al. . |
| 4,352,356 | 10/1982 | Tong ................................ 128/288 |
| 4,355,425 | 10/1982 | Jones et al. ............................. 2/402 |
| 4,388,075 | 6/1983 | Mesek et al. ........................ 604/385 |
| 4,397,645 | 8/1983 | Buell ................................... 604/380 |
| 4,407,284 | 10/1983 | Pieniak ................................ 604/385 |
| 4,413,996 | 11/1983 | Taylor ................................. 604/382 |

| Patent No. | Date | Inventor | Class |
|---|---|---|---|
| 4,425,127 | 1/1984 | Suzuki et al. | 604/366 |
| 4,425,128 | 1/1984 | Motomura | 604/381 |
| 4,425,173 | 1/1984 | Frick | 156/204 |
| 4,427,408 | 1/1984 | Karami et al. | 604/393 |
| 4,430,086 | 2/1984 | Repke | 604/385 |
| 4,486,192 | 12/1984 | Sigl | 604/385 |
| 4,488,927 | 12/1984 | Hooper . | |
| 4,490,148 | 12/1984 | Beckestrom . | |
| 4,496,359 | 1/1985 | Pigneul . | |
| 4,496,360 | 1/1985 | Joffe et al. . | |
| 4,498,944 | 2/1985 | Krause et al. . | |
| 4,500,316 | 2/1985 | Damico . | |
| 4,501,587 | 2/1985 | Enloe . | |
| 4,527,989 | 7/1985 | Karami . | |
| 4,555,245 | 11/1985 | Armbruster . | |
| 4,560,380 | 12/1985 | Tharel . | |
| 4,578,071 | 3/1986 | Buell . | |
| 4,578,073 | 3/1986 | Dysart et al. . | |
| 4,579,556 | 4/1986 | McFarland . | |
| 4,589,876 | 5/1986 | Van Tilburg . | |
| 4,597,760 | 7/1986 | Buell . | |
| 4,597,761 | 7/1986 | Buell . | |
| 4,601,717 | 7/1986 | Blevins . | |
| 4,610,680 | 9/1986 | LaFleur . | |
| 4,610,681 | 9/1986 | Strohbeen et al. . | |
| 4,619,649 | 10/1986 | Roberts . | |
| 4,623,342 | 11/1986 | Ito et al. . | |
| 4,626,305 | 12/1986 | Suzuki et al. . | |
| 4,630,320 | 12/1986 | Van Gompel . | |
| 4,639,949 | 2/1987 | Ales et al. . | |
| 4,641,381 | 2/1987 | Heran et al. . | |
| 4,642,819 | 2/1987 | Ales et al. . | |
| 4,646,362 | 3/1987 | Heran et al. . | |
| 4,655,760 | 4/1987 | Morman et al. . | |
| 4,657,539 | 4/1987 | Hasse . | |
| 4,661,102 | 4/1987 | Shikata et al. . | |
| 4,662,877 | 5/1987 | Williams . | |
| 4,671,793 | 6/1987 | Hults et al. . | |
| 4,681,579 | 7/1987 | Toussant et al. . | |
| 4,687,477 | 8/1987 | Suzuki et al. . | |
| 4,687,478 | 8/1987 | Van Tilburg . | |
| 4,690,681 | 9/1987 | Haunschild et al. . | |
| 4,692,163 | 9/1987 | Widlund et al. . | |
| 4,695,278 | 9/1987 | Lawson . | |
| 4,695,279 | 9/1987 | Steer . | |
| 4,701,171 | 10/1987 | Boland et al. . | |
| 4,701,177 | 10/1987 | Ellis et al. . | |
| 4,704,115 | 11/1987 | Buell . | |
| 4,704,116 | 11/1987 | Enloe . | |
| 4,710,187 | 12/1987 | Boland et al. . | |
| 4,718,902 | 1/1988 | Bonito . | |
| 4,735,622 | 4/1988 | Acuff et al. . | |
| 4,738,676 | 4/1988 | Osborn, III . | |
| 4,738,677 | 4/1988 | Foreman . | |
| 4,743,239 | 5/1988 | Cole . | |
| 4,743,241 | 5/1988 | Igaue et al. . | |
| 4,743,246 | 5/1988 | Lawson . | |
| 4,745,636 | 5/1988 | Lunt . | |
| 4,747,846 | 5/1988 | Boland et al. . | |
| 4,753,646 | 6/1988 | Enloe . | |
| 4,762,521 | 8/1988 | Roessler et al. . | |
| 4,775,375 | 10/1988 | Aledo . | |
| 4,795,452 | 1/1989 | Blaney et al. . | |
| 4,795,454 | 1/1989 | Dragoo . | |
| 4,798,603 | 1/1989 | Meyer et al. . | |
| 4,808,177 | 2/1989 | DesMarais et al. . | |
| 4,808,178 | 2/1989 | Aziz et al. . | |
| 4,816,025 | 3/1989 | Foreman . | |
| 4,816,026 | 3/1989 | Richardson . | |
| 4,822,435 | 4/1989 | Igaue et al. . | |
| 4,834,740 | 5/1989 | Suzuki et al. . | |
| 4,846,823 | 7/1989 | Enloe . | |
| 4,846,825 | 7/1989 | Enloe et al. . | |
| 4,850,990 | 7/1989 | Huntoon et al. . | |
| 4,861,652 | 8/1989 | Lippert et al. . | |
| 4,880,420 | 11/1989 | Pomparelli . | |
| 4,883,480 | 11/1989 | Huffman et al. . | |
| 4,883,482 | 11/1989 | Gandrez et al. . | |
| 4,892,528 | 1/1990 | Suzuki et al. . | |
| 4,895,568 | 1/1990 | Enloe . | |
| 4,900,317 | 2/1990 | Buell . | |
| 4,904,251 | 2/1990 | Igaue et al. . | |
| 4,909,803 | 3/1990 | Aziz et al. . | |
| 4,909,804 | 3/1990 | Douglas, Sr. . | |
| 4,916,005 | 4/1990 | Lippert et al. . | |
| 4,917,696 | 4/1990 | De Jonckheere . | |
| 4,938,753 | 7/1990 | Van Gompel et al. . | |
| 4,938,754 | 7/1990 | Mesek . | |
| 4,938,755 | 7/1990 | Foreman . | |
| 4,938,757 | 7/1990 | Van Gompel et al. . | |
| 4,940,464 | 7/1990 | Van Gompel et al. . | |
| 4,988,344 | 1/1991 | Reising et al. . | |
| 5,021,051 | 6/1991 | Hiuke . | |
| 5,030,303 | 7/1991 | Cucuzza . | |
| 5,032,120 | 7/1991 | Freeland et al. . | |
| 5,080,658 | 1/1992 | Igaue et al. . | |
| 5,085,654 | 2/1992 | Buell . | |
| 5,087,255 | 2/1992 | Sims . | |
| 5,114,420 | 5/1992 | Igaue et al. . | |
| 5,167,653 | 12/1992 | Igaue et al. . | |
| 5,188,627 | 2/1993 | Igaue et al. . | |
| 5,190,606 | 3/1993 | Merkatoris et al. . | |
| 5,236,430 | 8/1993 | Bridges . | |
| 5,246,431 | 9/1993 | Minetola et al. . | |
| 5,246,432 | 9/1993 | Suzuki et al. . | |
| 5,246,433 | 9/1993 | Hasse et al. . | |
| B1 4,636,207 | 11/1989 | Buell . | |

FOREIGN PATENT DOCUMENTS

| | | |
|---|---|---|
| 0329160A2 | 8/1989 | European Pat. Off. . |
| 0346477B1 | 12/1989 | European Pat. Off. . |
| 0374640A2 | 6/1990 | European Pat. Off. . |
| 0376022A2 | 7/1990 | European Pat. Off. . |
| 0386815A2 | 9/1990 | European Pat. Off. . |
| 0391476A2 | 10/1990 | European Pat. Off. . |
| 0409149A1 | 1/1991 | European Pat. Off. . |
| 0456885A1 | 11/1991 | European Pat. Off. . |
| 0263720B1 | 12/1991 | European Pat. Off. . |
| 0539703A1 | 5/1993 | European Pat. Off. . |
| 0549988A1 | 7/1993 | European Pat. Off. . |
| 2425205 | 12/1979 | France . |
| 2554325 | 5/1985 | France . |
| 2557774 | 7/1985 | France . |
| 2561078 | 9/1985 | France . |
| 2573629 | 5/1986 | France . |
| 1070779 | 12/1959 | Germany . |
| 1435861 | 2/1969 | Germany . |
| 2455778 | 6/1975 | Germany . |
| 2521621 | 12/1975 | Germany . |
| 2629560 | 1/1977 | Germany . |
| 3039940A1 | 6/1981 | Germany . |
| 3216170A1 | 12/1982 | Germany . |
| 2454590C2 | 1/1983 | Germany . |
| 3319043A1 | 11/1984 | Germany . |
| 3439775A1 | 5/1985 | Germany . |
| 2521621C2 | 10/1985 | Germany . |
| 2657220C2 | 3/1987 | Germany . |
| 2657221C2 | 3/1987 | Germany . |
| 3141963C2 | 7/1988 | Germany . |
| 3128828C2 | 11/1989 | Germany . |
| 41-18359 | 8/1966 | Japan . |
| 41-18031 | 8/1976 | Japan . |
| 63-12702 | 1/1988 | Japan . |
| 63-12705 | 1/1988 | Japan . |

| Number | Date | Country |
|---|---|---|
| 63-21901 | 1/1988 | Japan . |
| 63-105102 | 5/1988 | Japan . |
| 63-112706 | 5/1988 | Japan . |
| 63-112705 | 5/1988 | Japan . |
| 63-112703 | 5/1988 | Japan . |
| 63-112702 | 5/1988 | Japan . |
| 63-190002 | 8/1988 | Japan . |
| 63-230164 | 9/1988 | Japan . |
| 64-18105 | 1/1989 | Japan . |
| 64-18106 | 1/1989 | Japan . |
| 64-26701 | 1/1989 | Japan . |
| 64-26310 | 2/1989 | Japan . |
| 64-68503 | 3/1989 | Japan . |
| 64-77607 | 3/1989 | Japan . |
| 1-162808 | 6/1989 | Japan . |
| 1-162807 | 6/1989 | Japan . |
| 1-162806 | 6/1989 | Japan . |
| 1-183501 | 7/1989 | Japan . |
| 1-168903 | 7/1989 | Japan . |
| 1-213402 | 8/1989 | Japan . |
| 1-246402 | 10/1989 | Japan . |
| 1-173106 | 12/1989 | Japan . |
| 2-65861 | 3/1990 | Japan . |
| 2-65859 | 3/1990 | Japan . |
| 2-58426 | 4/1990 | Japan . |
| 2-58425 | 4/1990 | Japan . |
| 2-58427 | 4/1990 | Japan . |
| 2-107249 | 4/1990 | Japan . |
| 2-71521 | 5/1990 | Japan . |
| 2-63834 | 5/1990 | Japan . |
| 2-142565 | 5/1990 | Japan . |
| 2-142564 | 5/1990 | Japan . |
| 2-126850 | 5/1990 | Japan . |
| 2-164361 | 6/1990 | Japan . |
| 2-164362 | 6/1990 | Japan . |
| 2-156946 | 6/1990 | Japan . |
| 2-152450 | 6/1990 | Japan . |
| 2-152451 | 6/1990 | Japan . |
| 2-152452 | 6/1990 | Japan . |
| 2-191452 | 7/1990 | Japan . |
| 2-174845 | 7/1990 | Japan . |
| 2-84623 | 7/1990 | Japan . |
| 2-274250 | 11/1990 | Japan . |
| 2-271863 | 11/1990 | Japan . |
| 3-21238 | 1/1991 | Japan . |
| 3-4850 | 1/1991 | Japan . |
| 3-59 | 1/1991 | Japan . |
| 3-224558 | 3/1991 | Japan . |
| 3-24118 | 3/1991 | Japan . |
| 3-60656 | 3/1991 | Japan . |
| 3-90149 | 4/1991 | Japan . |
| 3-80858 | 4/1991 | Japan . |
| 3-123553 | 5/1991 | Japan . |
| 3-121069 | 5/1991 | Japan . |
| 3-111048 | 5/1991 | Japan . |
| 3-136655 | 6/1991 | Japan . |
| 3-143443 | 6/1991 | Japan . |
| 3-136653 | 6/1991 | Japan . |
| 3-133452 | 6/1991 | Japan . |
| 3-131253 | 6/1991 | Japan . |
| 3-151970 | 6/1991 | Japan . |
| 3-60919 | 6/1991 | Japan . |
| 3-165761 | 7/1991 | Japan . |
| 3-198851 | 8/1991 | Japan . |
| 3-188851 | 8/1991 | Japan . |
| 3-186262 | 8/1991 | Japan . |
| 3-186261 | 8/1991 | Japan . |
| 3-218752 | 9/1991 | Japan . |
| 3-202054 | 9/1991 | Japan . |
| 3-207358 | 9/1991 | Japan . |
| 3-234257 | 10/1991 | Japan . |
| 3-231660 | 10/1991 | Japan . |
| 3-101935 | 10/1991 | Japan . |
| 3-268753 | 11/1991 | Japan . |
| 3-286760 | 12/1991 | Japan . |
| 3-280951 | 12/1991 | Japan . |
| 4-5825 | 1/1992 | Japan . |
| 4-22359 | 1/1992 | Japan . |
| 4-9153 | 1/1992 | Japan . |
| 4-92665 | 3/1992 | Japan . |
| 4-67864 | 3/1992 | Japan . |
| 4-40625 | 4/1992 | Japan . |
| 4-122256 | 4/1992 | Japan . |
| 4-42815 | 4/1992 | Japan . |
| 4-42816 | 4/1992 | Japan . |
| 4-47428 | 4/1992 | Japan . |
| 4-152947 | 5/1992 | Japan . |
| 4-150853 | 5/1992 | Japan . |
| 4-200543 | 7/1992 | Japan . |
| 4-218157 | 8/1992 | Japan . |
| 4-218159 | 8/1992 | Japan . |
| 4-224750 | 8/1992 | Japan . |
| 4-90322 | 8/1992 | Japan . |
| 4-99921 | 8/1992 | Japan . |
| 4-295356 | 10/1992 | Japan . |
| 4-120731 | 10/1992 | Japan . |
| 4-325153 | 11/1992 | Japan . |
| 5-184622 | 7/1993 | Japan . |
| 5-84322 | 11/1993 | Japan . |
| 358765 | 10/1931 | United Kingdom . |
| 667483 | 3/1952 | United Kingdom . |
| 790062 | 2/1958 | United Kingdom . |
| 849573 | 9/1960 | United Kingdom . |
| 1428572 | 3/1976 | United Kingdom . |
| 1453870 | 10/1976 | United Kingdom . |
| 1482677 | 8/1977 | United Kingdom . |
| 1520740 | 8/1978 | United Kingdom . |
| 1520017 | 8/1978 | United Kingdom . |
| 1520018 | 8/1978 | United Kingdom . |
| 1543915 | 4/1979 | United Kingdom . |
| 2023431 | 1/1980 | United Kingdom . |
| 2051557 | 1/1981 | United Kingdom . |
| 2063677 | 6/1981 | United Kingdom . |
| 2080093 | 2/1982 | United Kingdom . |
| 2101468 | 1/1983 | United Kingdom . |
| 2103093 | 2/1983 | United Kingdom . |
| 2149289 | 6/1985 | United Kingdom . |
| 2159693 | 12/1985 | United Kingdom . |
| 2161059 | 1/1986 | United Kingdom . |
| 2188532 | 10/1987 | United Kingdom . |
| 2193625 | 2/1988 | United Kingdom . |
| 2196834 | 5/1988 | United Kingdom . |
| 2197181 | 5/1988 | United Kingdom . |
| 2215986 | 4/1989 | United Kingdom . |
| 2212382 | 7/1989 | United Kingdom . |
| 2216393 | 10/1989 | United Kingdom . |
| 2241871 | 9/1991 | United Kingdom . |
| 2242610 | 10/1991 | United Kingdom . |
| 2244422 | 12/1991 | United Kingdom . |
| 2266225 | 4/1992 | United Kingdom . |
| 2250921 | 6/1992 | United Kingdom . |
| 2251172 | 7/1992 | United Kingdom . |
| 2270247 | 9/1992 | United Kingdom . |
| 2255896 | 11/1992 | United Kingdom . |
| 2265834 | 10/1993 | United Kingdom . |
| 2268389 | 1/1994 | United Kingdom . |
| WO88/05269 | 7/1988 | WIPO . |
| WO90/14063 | 11/1990 | WIPO . |
| WO92/07533 | 5/1992 | WIPO . |
| WO93/09739 | 5/1993 | WIPO . |
| WO93/09742 | 5/1993 | WIPO . |
| WO93/09746 | 5/1993 | WIPO . |
| WO93/17648 | 9/1993 | WIPO . |

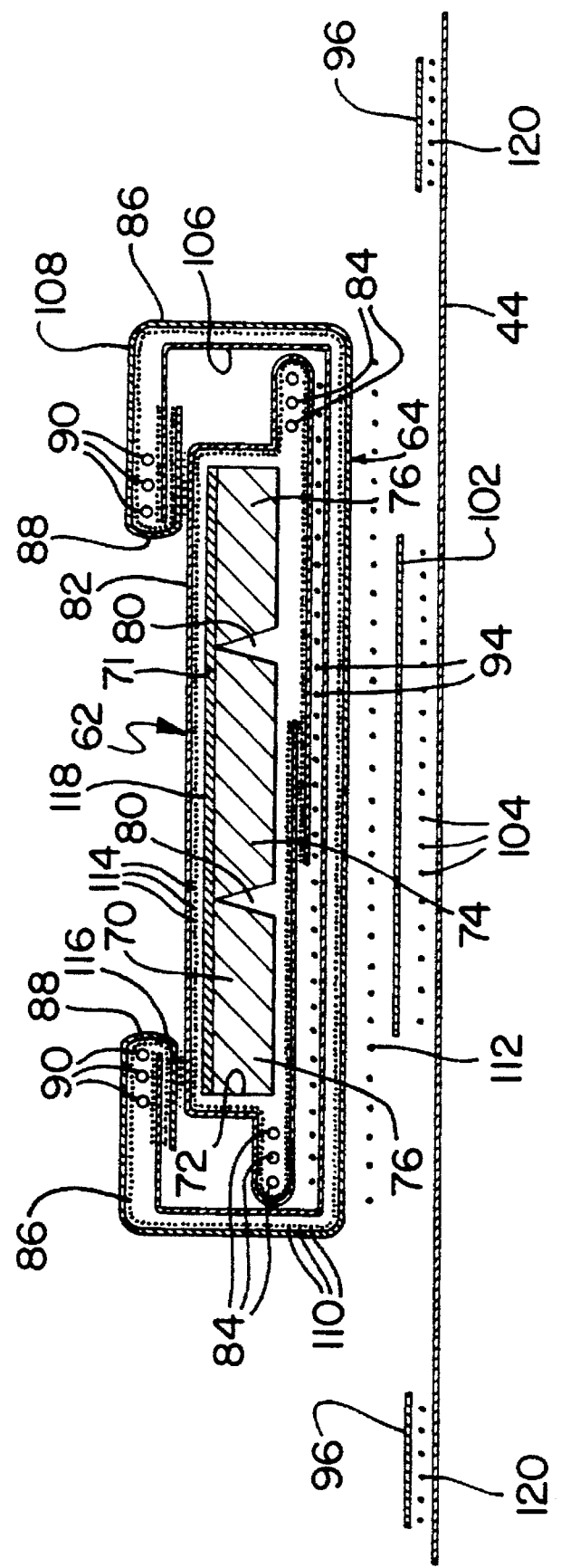

CHILD'S TRAINING PANT WITH ELASTICIZED SHAPED ABSORBENT AND METHOD OF MAKING THE SAME

BACKGROUND OF THE INVENTION

This invention pertains to disposable absorbent articles, and more particularly to a child's disposable absorbent training pant having an elasticized three-dimensional absorbent for improving the containment of waste.

Various disposable absorbent articles exist today for absorbing waste material of infants and small children. One of these is a disposable diaper that is fitted on the baby by the mother or caretaker. Because an adult is doing the fitting, the diaper, in most cases, will be properly fitted on the baby. This is an advantage for the designers of diapers since they can design an absorbent crotch that is relatively wide and flat, in relation to the baby's crotch, to improve containment, and still have the assurance that the adult will properly fit the diaper at the baby's crotch.

In contrast to babies and their diapers, children in the potty training stage and their training pants pose a different scenario. One difference is that these children put on their own training pant, which means that they are the ones responsible for ensuring the pant is properly positioned. As most parents discover, their children are not as careful in or capable of correctly donning the training pant. This results in the training pant sometimes being worn in a twisted or turned condition at the waist and crotch, or not being pulled up to the waist sufficiently to properly fit the absorbent crotch against the wearer. Sometimes the training pant is even put on backwards.

Another problem is that a training pant having a relatively wide and flat absorbent crotch, such as that found in a typical diaper, further exacerbates the problem of an ill-fit. The situation in which a child pulls the pant upwardly in a twisted or turned fashion, or backwards, not only results in improper alignment of the absorbent with the body, but also results in a deformation of the absorbent at the crotch. The deformed absorbent generally will assume the shape of an inverted-U in the crotch. This has an extremely negative impact on the performance of the absorbent. The inverted-U shape tends to cause liquid waste to flow towards either one or both sides of the absorbent, thereby creating pools of waste at the area of least absorbent capacity and highest probability of leaking.

Another difference between the use of a diaper and training pant is that the child wearing a training pant is much more mobile and active than a baby, and this will increase the tendency or chances of a training pant to move out of the correct position.

One attempt to address the above problems was to form the absorbent crotch portion of the training pant more narrow than that of a diaper absorbent crotch portion. This was intended to make the training pant easier to pull up and properly position at the crotch of the wearer. It was also hoped that this would assist or maintain the pant in the proper position during various physical activities of the wearer. However, this attempt was not entirely successful, and posed an additional problem of having a greater tendency of leaking due to the lesser amount of absorbent material in the crotch area, and increasing the possibility of the narrower absorbent crotch portion to be off-center relative to the point of urination.

SUMMARY OF THE INVENTION

In one form of the present invention, there is provided a disposable absorbent child's training pant including a generally liquid permeable pant body having a front waist section, a back waist section, a crotch section, a waist opening, and a pair of leg openings; an absorbent composite disposed in the pant body at least at the crotch section, and including a longitudinally extending absorbent central portion and a pair of longitudinally extending absorbent side portions; a weakened area between each absorbent side portion and the absorbent central portion; a liquid impermeable layer disposed between the absorbent composite and the pant body, and including a pair of longitudinally extending side flaps having respective flap distal edges; and a flap elastic member elastically associated with each flap distal edge.

In another form of the present invention there is provided a disposable absorbent pant including a pant body having an interior space, a waist opening, a pair of leg openings, and a crotch section; an absorbent composite disposed in the interior space at the crotch section and including an absorbent central portion and a pair of absorbent side portions; a weakened area between each absorbent side portion and the absorbent central portion; a layer disposed between the absorbent composite and the pant body and including a pair of side flaps having respective distal edges extending laterally beyond the absorbent side portions; and a flap elastic member elastically associated with each flap distal edge.

In still another form of the present invention there is provided a disposable absorbent article comprising a backsheet; an absorbent composite on the backsheet and including a pair of longitudinally extending absorbent side portions; a weakened area between the absorbent side portions; a layer disposed between the absorbent composite and the backsheet and including a pair of longitudinally extending side flaps having respective flap distal edges extending laterally beyond the absorbent side portions; and a flap elastic member elastically associated with each flap distal edge.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein:

FIG. 10 illustrates an elevational, exploded, end view of the form illustrated in FIG. 9.

DEFINITIONS

Within the context of this specification, each term or phrase below will include the following meaning or meanings:

(a) "Member" when used in the singular can have the dual meaning of a single element or a plurality of elements.

(b) "Disposed" and variations or uses thereof are intended to mean that one element can be integral with another element, or that one element can be a separate structure joined to or connected to or placed with or placed near another element.

(c) "Elastically associated" with reference to the attachment of an elastic member to another element means that the elastic member when attached to or placed with the element gives that element elastic properties. The attaching or placing can be either directly, such as attaching or placing the member directly with the element, or can be indirectly by means of another member or element between the first member and the first element.

(d) "Disposable" includes being disposed of after use, and not intended to be washed and reused.

(e) "Elasticity", "elasticized", and "elastic" include that property of a material by virtue of which it tends to recover its original size and shape after removal of a force causing the deformation.

(f) "Associated with" in reference to two or more elements means that the elements can be attached or placed together in any suitable manner that allows them to perform the intended or described function, while not completely inhibiting the properties of the individual elements.

(g) "Stretch-bonded laminate", "SBL", and variations thereof mean at least a two-layered composite in which one layer is a gatherable layer and the other layer is an elastic layer. The layers are joined together when the elastic layer is in a stretched condition so that, upon relaxing the layers, the gatherable layer is gathered and the elastic layer is relaxed, non-gathered.

(h) "Three-dimensional" refers to a finished garment similar to shorts or pants in that they have leg openings and a waist opening that are continuous, i.e., are bounded by the material of which they are made. This type of garment can be opened and laid flat only by destructively tearing it. This type of garment may or may not have manually tearable seams.

These terms may be further defined with additional language in the remaining portion of the specification.

DESCRIPTION OF A PREFERRED EMBODIMENT

Figure 1:
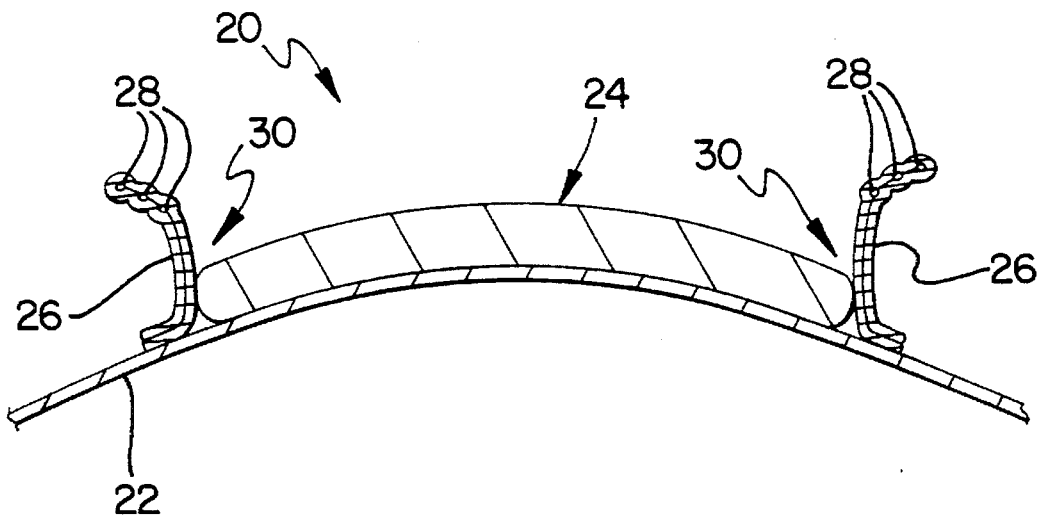
FIG. 1 illustrates a fragmented front elevational view in cross section of the absorbent crotch portion of a conventional disposable article.

Referring to FIG. 1, there is illustrated conventional disposable article 20 comprising backsheet 22 having absorbent structure 24 attached thereto, and a pair of containment flaps 26 having respective flap elastics 28 for gathering flaps 26. Because of the relatively large width of about 4 inches to about 8 inches of absorbent structure 24, compared to the width of about 1½ inches to about 3 inches of the wearer's crotch, as article 20 is fitted on the wearer, the absorbent structure 24 tends to form a generally inverted U-shape, and containment flaps 26 begin to turn or bend downwardly and outwardly. The inverting and bending actions are due in major part to the fact that a relatively wide absorbent structure is being forcibly fitted into a relatively narrow space, i.e., the wearer's crotch. This results in pooling areas 30 formed by the downwardly-oriented sides of absorbent structure 24 and containment flaps 26. These pooling areas 30 greatly increase the probability of liquid leaking over containment flaps 26 and against the wearer; not the performance desired of any absorbent article.

The present invention provides improved waste containment by controlling the deformation or the inverting-action of these types of relatively wide absorbent structures or composites as they are being fitted on the wearer and during movement of the wearer. By controlling the deformation or inverting of the absorbent structures or composites, the present invention permits an increased or larger absorbent surface area to be properly fitted in the narrow confines of the crotch in a comfortable manner. In addition, by controlling the deformation and creating a shaped absorbent structure, thinner and wider absorbent composites can be incorporated into the absorbent article or product. This combination of thinness and superior urine containment performance is particularly desired for disposable absorbent training pants. The increase in absorbent surface area promotes improved coverage and absorbency in the area of the point of urination, thereby enhancing containment performance.

Referring to FIGS. 3–6, and 9, there is illustrated a training pant 32 incorporating the principles of the present invention. It should be understood that other disposable pant-like or three-dimensional absorbent articles may also incorporate these same principles. Training pant 32 comprises a pant body 34 having a waist opening 36, leg openings 38, and an interior space 40, for fitting training pant 32 on the body 42 of a wearer. Pant body 34 is formed from a backsheet 44 of material that desirably is both liquid permeable and elastic. One material of which backsheet 44 can be made is a liquid permeable nonwoven web having a basis weight of about 27 grams per square meter (gsm), and which can be formed from spunbond bicomponent fibers or by carding bicomponent fibers. Suitable bicomponent fibers are wettable, polyethylene/polypropylene bicomponent fibers available from CHISSO Corporation, PP Fiber Division, 6-32, Nakanoshima 3, Kita-Ku, Osaka, Japan. In this particular material, the polypropylene forms the core and the polyethylene forms the sheath of the composite fiber.

Backsheet 44 can be made of other suitable liquid permeable materials. One example is a liquid permeable spunbond polypropylene nonwoven web having a basis weight of about 27 gsm.

Another example includes two layers of a spunbond polypropylene nonwoven web, each web having a basis weight of about 27 gsm, with multiple strands of LYCRA® 940 decitex adhered under a selected tension between the spunbond polypropylene nonwoven webs. A similar two-layer composite can be made with spunbond bicomponent fibrous webs in place of the spunbond polypropylene webs.

Still another example is a backsheet 44 made of a stretchable or elastic material that is also liquid permeable, such as a stretch-bonded laminate, or a single layer of elastic material. The stretch-bonded laminate can comprise an inner layer of a prestretched elastic meltblown material sandwiched between and attached to a pair of spunbond polypropylene nonwoven webs, in which the webs have basis weights of about 14 gsm. Suitable elastic materials can be purchased from the Shell Chemical Company, Houston, Tex., under the trademark KRATON®.

The present invention contemplates that backsheet 44 can be made of a liquid impermeable material that may or may not have elastic properties. One example of a non-elastic material is a 0.6 mil polyethylene film obtainable from Edison Plastics Company, South Plainfield, N.J.

Backsheet 44 can be a two-ply laminate in which the innermost layer can be the above-described liquid impermeable film or any other suitable liquid impermeable layer, and the outermost layer can be the above-described liquid permeable spunbond polypropylene nonwoven web or any other suitable liquid permeable layer. These layers can be joined together in any suitable manner.

Figure 3:
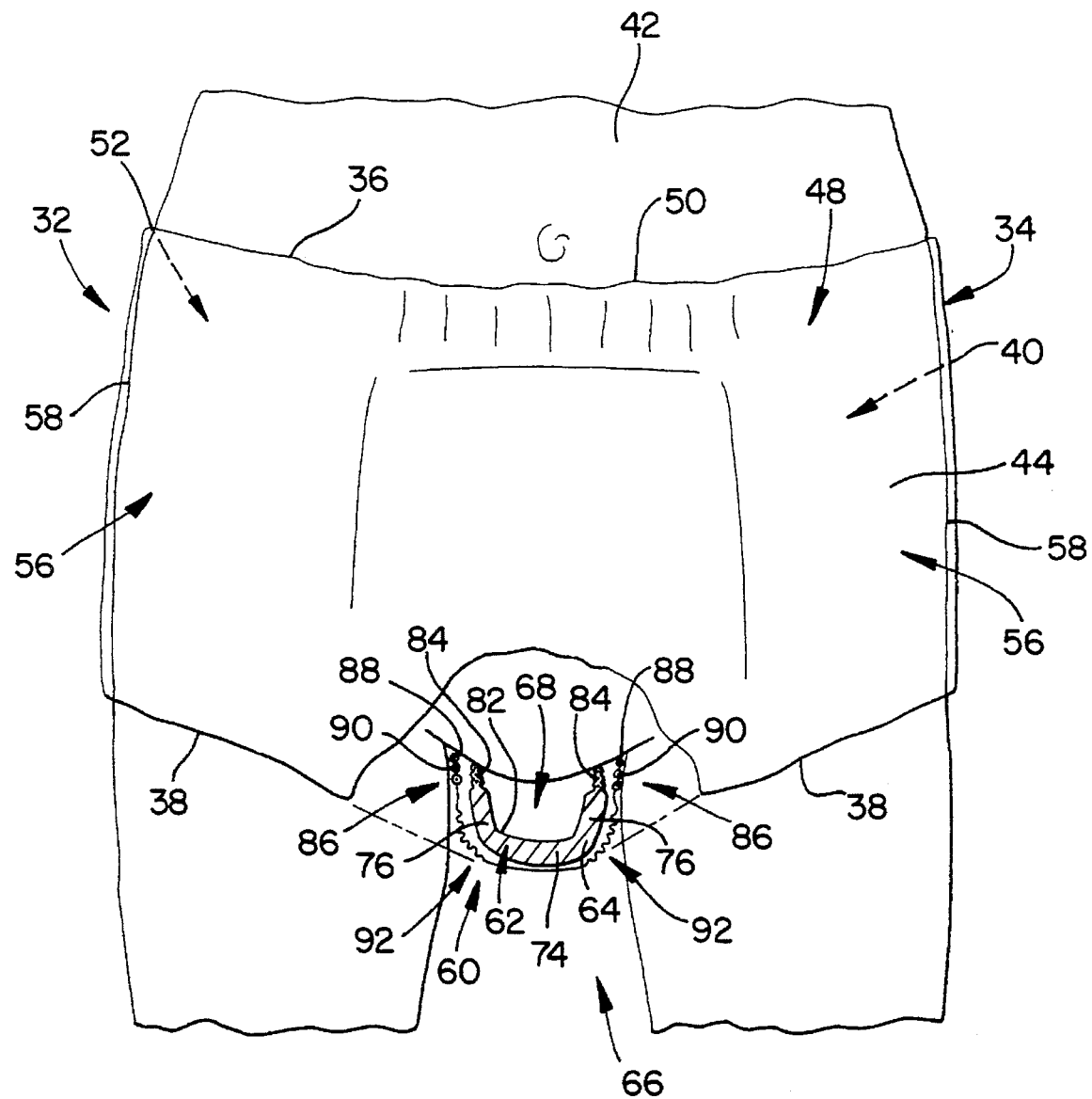
FIG. 3 illustrates a front elevational, partially broken-away view of a training pant incorporating the principles of the present invention.
Figure 9:
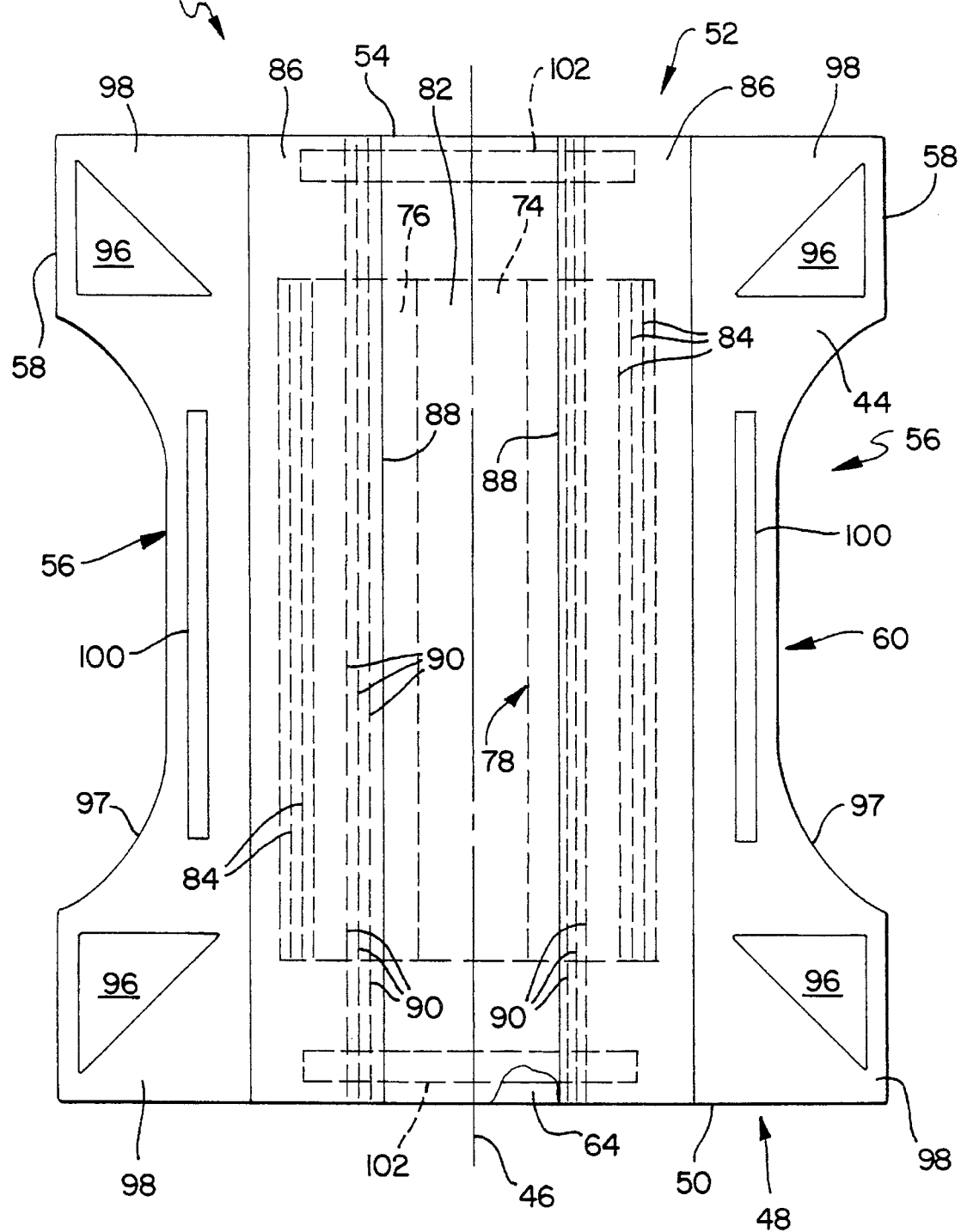
FIG. 9 illustrates a top elevational view of the form in FIG. 7 in a partially disassembled, stretched flat training pant.

Referring primarily to FIG. 9, backsheet 44 is illustrated in an opened, stretched-flat condition with a longitudinal centerline 46, and includes front waist section 48 having front edge 50, back waist section 52 having back edge 54, side sections 56 having respective side edges 58, and a crotch section 60. By folding backsheet 44 along a fold line that is generally perpendicular to longitudinal centerline 46, and then bonding the end portions, such as ears 98, of each side section 56 together, pant body 34 is formed having waist opening 36, leg openings 38, and interior space 40 (FIG. 3). One method of forming a pant body 34 and a training pant 32 is described in greater detail in U.S. Pat. No. 4,940,464, which is assigned to the assignee of the present invention, the contents of which are incorporated by reference herein.

Still referring to FIG. 9, the use of the term "longitudinally extending" or variations thereof with reference to an element means that the element extends in a direction generally parallel to longitudinal centerline 46. The term "laterally" or "transversely" refers to a direction that is generally perpendicular to longitudinal centerline 46.

Unique features of the present invention are illustrated in various forms with reference to FIGS. 2, 5–6, and 7–8. These figures typify three specific forms of the present invention, but it is understood that other forms can be designed and manufactured in accordance with the principles of the present invention. The following description is made with reference to FIGS. 3–6.

Figure 5:
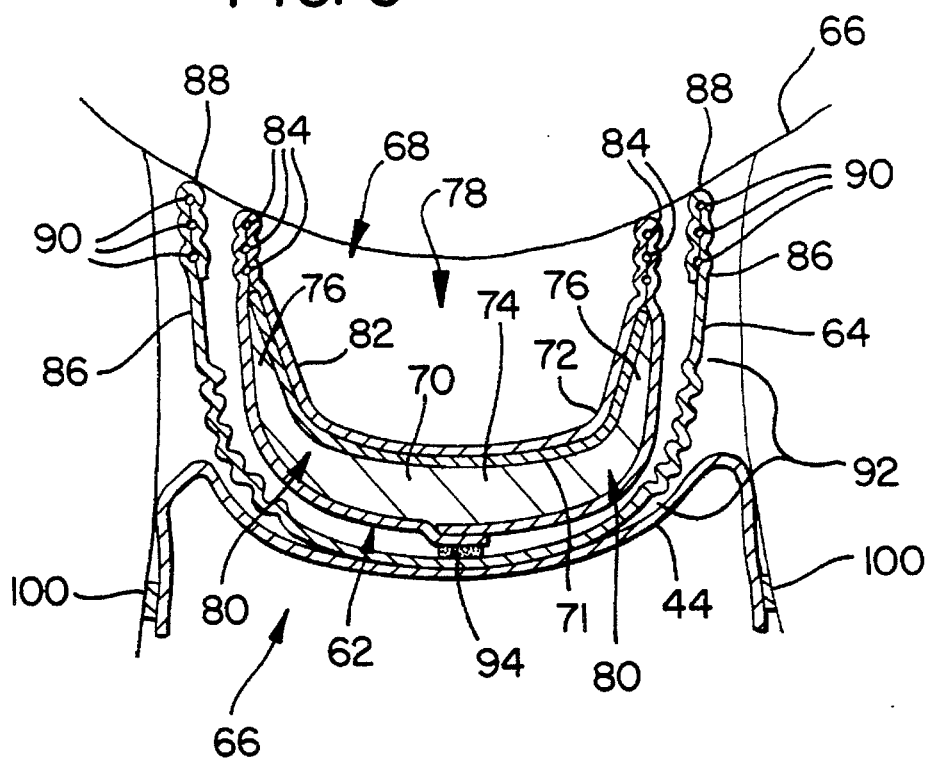
FIG. 5 illustrates a front elevational view in cross section of another form of the present invention in the crotch of a wearer.

FIG. 5 illustrates absorbent composite 62 and a layer 64 of material, desirably liquid impermeable, forming a generally longitudinally extending containment channel 68 in the crotch 66 of the wearer. Containment channel 68 has a length dimension greater than the width dimension, and extends between the legs of the wearer sufficiently to form an elongated space between the crotch 66 and absorbent composite 62. As illustrated in FIG. 5, absorbent composite 62 is unloaded, i.e., dry, which means that it has not absorbed any appreciable amounts of liquid waste material. Absorbent composite 62 can comprise any suitable absorbent material, as well as combinations of different types of absorbent material. Composite 62 desirably comprises a mixture 70 of fluff and superabsorbent material (SAM) wrapped in a liquid permeable tissue wrap 72. Suitable superabsorbent materials include inorganic materials such as silica gels or organic compounds such as cross-linked polymers. Examples include polyacrylamides, polyvinyl alcohol, polyacrylates, various grafted starches, and the like. A desired superabsorbent material is a cross-linked polysodium acrylate, which can be purchased from Hoechst-Celanese, Portsmouth, Va. The superabsorbent materials can be in various geometric forms, such as various shaped particles, fibers, foams, and layers. The mixture 70 of fluff and SAM is generally rectangular in shape, and in one particular shape has a length of about 38 cm and a width of about 11 cm. The fluff and SAM are present in a ratio of about 10–12 grams fluff to about 10–12 grams SAM, and have a density within the range of about 0.20 grams per cubic centimeter to about 0.35 grams per cubic centimeter. A more detailed description of this particular absorbent can be found in U.S. patent application Ser. No. 08/096,654 filed Jul. 22, 1993, which is assigned to the assignee of this application, the contents of which are incorporated by reference herein.

The SAM is desirably deposited in the fluff such that more SAM is concentrated adjacent to or near backsheet 44. The mixture 70 can also be zoned, in that a greater amount of fluff and/or SAM can be located in the center of the absorbent composite 62 or toward the front or back of the composite. For example, a girl's training pant would generally have more absorbent zoned or concentrated at the longitudinal center of the absorbent composite, while a boy's training pant would have more absorbent zoned or concentrated at a position intermediate the longitudinal center and the front edge of the composite. It should also be understood that the fluff and SAM can be mixed in any desirable fashion or concentration, and that the SAM can exist as a discrete layer anywhere within the fluff, or on top of or below the fluff.

Absorbent composite 62 can be a single, integral absorbent structure, or can comprise a plurality of individual, separate absorbent structures and/or absorbent materials that are operably assembled together. If absorbent composite 62 comprises multiple structures, the structures can be configured as discrete layered or non-layered shapes and configurations. Furthermore, the individual structures can be coextensive or non-coextensive. It is desired that each individual absorbent structure be arranged in operable, intimate contact along at least a portion of its boundary with at least one other adjacent absorbent structure.

Absorbent composite 62 further can be an air-laid nonwoven web comprising about 80 percent by weight fibrous superabsorbent material and about 20 percent by weight polymeric binder fiber. The fibrous superabsorbent materials have a denier of about 9 d and a length of about 12 millimeters. Suitable fibrous superabsorbent materials are available from Technical Absorbents Ltd. of the United Kingdom under the tradename OASIS. The polymeric binder fibers have a denier of about 3 d and a length of about 6 millimeters. Such binder fibers may be bicomponent fibers comprising about 50 percent by weight polyethylene and about 50 percent by weight polypropylene in a concentric sheath configuration. Suitable bicomponent binder fibers are available from Danaklon a/s of Varde, Denmark, under the tradename DANAKLON AL Thermo-C. Such a composite web may be oven used after air-laying for five minutes at a temperature of about 150 degrees celsius. The composite web may have a basis weight of about 200 grams per square meter.

A surge layer 71 can be disposed between absorbent composite 62 and permeable layer 82, or on top of permeable layer 82, to improve the absorbency of composite 62. Surge layer 71 serves to manage, transport, accommodate, and/or direct high volumes and high flow rates of urine into absorbent composite 62. Surge layer 71 desirably extends the total width, i.e., transverse dimension, of absorbent composite 62. Surge layer 71 can be a through-air, bonded carded web, a spunbond bicomponent nonwoven web, a web of cross-linked cellulosic fibers, or the like. Surge layer 71 can have an overall basis weight of about 50 gsm and an overall density of about 0.03 grams per cubic centimeter. Surge layer 71 can be a two-layered composite in which the first layer, which is the layer that will be adjacent the wearer's body, is a 15 gsm layer composed of 100 percent polyethylene/polyester, sheath-core bicomponent fibers having a fiber denier of about 1.8 to about 3 denier (d). The second layer, which is the outermost layer in the composite, is a 35 gsm layer composed of a mixture of bicomponent fibers and single component fibers. The bicomponent fibers form about 40 percent by weight of the outermost layer. More particularly, 35 percent by weight of the outermost layer is composed of about 1.8 d polyethylene/polyester sheath core fibers with flat crimp, and about 5 percent by weight of the outermost layer is composed of about 2 d polyethylene/polypropylene sheath core fibers with helical crimp. The single component fibers form about 60 percent by weight of the outermost layer, and are about 6 denier polyester fibers configured with a flat crimp. The polyester fibers are not hollow core fibers. Surge layer 71 is permeable to liquid when compressed under loads experienced during the wear of the absorbent article. Descriptions of other suitable materials of which surge layer 71 can be made are described in the aforementioned and incorporated U.S. patent application Ser. No. 08/096,654. Suitable bicomponent fibers are available from CHISSO, Osaka, Japan.

Referring to FIGS. 5 and 9, absorbent composite 62 includes a longitudinally extending absorbent central portion 74, a pair of longitudinally extending absorbent side portions 76, and an absorbent crotch portion 78 (FIG. 9). The term "central" means to be intermediate of two spaced-apart positions or elements, which in the case of absorbent central portion 74 are the absorbent side portions 76. Absorbent central portion 74 and absorbent side portions 76 can have the same or different absorbent and/or physical characteristics. For example, absorbent central portion 74 can have a higher, lower, or the same basis weight as one of the absorbent side portions 76, or absorbent central portion 74 can have a higher, lower, or the same density as one of the absorbent side portions 76. Similarly, absorbent central portion 74 can have a higher, lower, or the same concentration of SAM as one of the absorbent side portions 76. Desirably, absorbent central portion 74 has a higher basis weight and a lower density than any one of the absorbent side portions 76. In addition, absorbent central portion 74 and absorbent side portions 76 can be made of different absorbent materials.

A unique feature of the present invention is weakened area 80 (FIG. 5) that extends longitudinally of absorbent composite 62. As illustrated in FIG. 5, there are two weakened areas 80 in absorbent composite 62 where the absorbent side portions 76 are turned or moved upwardly relative to absorbent central portion 74. The term "upwardly" is to be understood with reference to FIG. 5 in which absorbent central portion 74 is illustrated in a relatively flat or horizontal manner. Thus, with reference to absorbent central portion 74 in FIG. 5, absorbent side portions 76 are turned upwardly or vertically at an angle to absorbent central portion 74. This provides absorbent composite 62 with a shape that is important in enhancing its performance as an absorbent. Weakened area 80 can be continuous or discontinuous in order to allow absorbent side portions 76 to move upwardly relative to absorbent central portion 74, as illustrated in FIG. 5. A weakened area 80 can be provided by various methods. One method is to form absorbent composite 62 with tapering absorbent side portions 76 as illustrated in FIG. 5. For example, absorbent central portion 74 can have a generally uniform thickness, while an absorbent side portion 76 can taper in a converging manner in a direction away from absorbent central portion 74. Generally, the tapering will begin at least about 1 centimeter in from the longitudinal edge of an absorbent side portion 76, and preferably about 2 centimeters in from the longitudinal edge of an absorbent side portion 76. Absorbent composite 62 also can be of generally oval shape in transverse cross-section, in which absorbent central portion 74 has its greatest thickness along its longitudinal centerline.

Another method for providing weakened areas 80 is to form an absorbent composite 62 having its greatest thickness along the centerline 46 and along or near both of its longitudinal edges, with a lesser thickness between each longitudinal edge and centerline 46. In transverse cross-section, this would have an undulating appearance.

Figure 2:
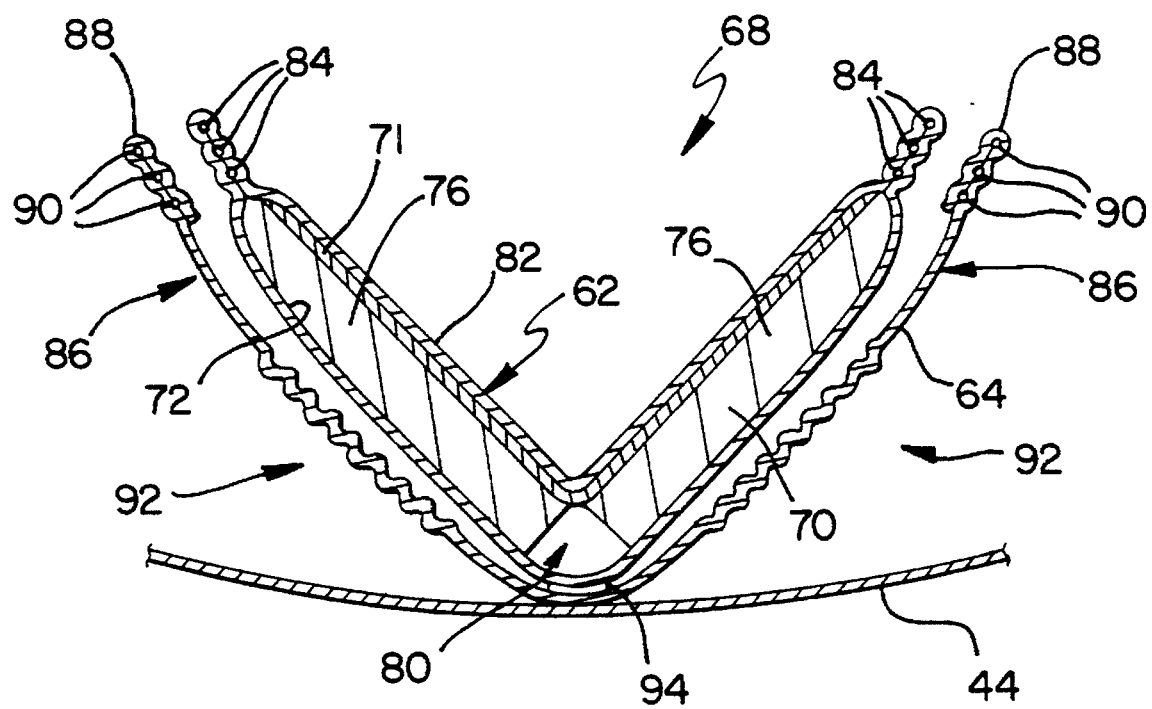
FIG. 2 illustrates a front elevational view in cross section of one form of the present invention.

Weakened area 80 can also be provided by longitudinally cutting absorbent composite 62, and then positioning absorbent side portions 76 in operable, intimate contact with each other (FIG. 2); in FIG. 2, there is no absorbent central portion 74. Rather than totally, separately cutting absorbent composite 62, a slit or score line (FIGS. 7 and 10) can be run along absorbent composite 62 to provide a weakened area 80 at which that particular absorbent side portion 76 can move upwardly relative to absorbent central portion 74. By slit or score is meant that absorbent composite 62 is cut in a fashion that does not totally separate an absorbent side portion 76 from absorbent central portion 74.

As described, the present invention thus contemplates the term "weakened area" to include any design, mechanism, or method that permits an absorbent side portion 76 to be movable upwardly. However, it should be understood that absorbent composite 62 can be designed or comprised of materials that permit it to be easily flexed or shaped without the necessity of a weakened area 80.

Continuing to refer to FIG. 5, absorbent composite 62 is enveloped by permeable layer 82. Layer 82 can be rendered permeable in numerous ways. For example, permeable layer 82 can be made of the same material and in the same manner as a liquid permeable backsheet 44. Also, layer 82 can be a film of liquid impermeable material rendered permeable by a multiplicity of apertures therethrough. However, it is desired that permeable layer 82 be a spunbonded polypropylene web having a basis weight of about 25 gsm. Layer 82 can be wrapped about absorbent composite 62 in any suitable manner well known in the art.

A pair of absorbent elastic members 84 are elastically associated with absorbent side portions 76. In FIG. 5, each absorbent elastic member 84 is just slightly spaced-apart from the longitudinal edge of its respective absorbent side portion 76 and is enveloped by permeable layer 82. Each absorbent elastic member 84 is desirably three strands of LYCRA® 940 decitex that are attached at their ends at an elongation of about 250 percent. Each individual strand in a respective absorbent elastic member 84 is spaced from another adjacent elastic strand by about 3 mm distance. These elastic strands can be obtained from E. I. DuPont De Nemours Company, Wilmington, Del. Each absorbent elastic member 84 can be one or more strands of the above described elastic, or can be made of other suitable elastic materials such as natural rubber, synthetic rubber, or thermoplastic elastomeric polymers. These elastic materials may also be heat-shrinkable or heat-elasticizable, and can also be a single ribbon of elastic material. Layer 82 also can be totally or partially elastic or stretchable. The direction of stretch can be in the longitudinal direction, transverse direction, or in multiple directions. Generally, the direction of stretch is determined during the manufacturing of the elastomeric material, and is related to the molecular orientation of the manufactured material. Suitable elastic materials are described in the aforementioned and incorporated U.S. Pat. No. 4,940,464.

FIG. 5 illustrates each absorbent elastic member 84 as being spaced-apart from its respective absorbent side portion 76, but the present invention contemplates that each absorbent elastic member 84 can be in other positions relative to its respective absorbent side portion 76. For example, an absorbent elastic member 84 can be positioned underneath or on top of its respective absorbent side portion 76. In any specific placement and attachment, absorbent elastic members 84, upon being relaxed, will tend to urge an absorbent side portion 76 upwardly relative to absorbent central portion 74, as described above. Alternatively, if desired, absorbent elastic members 84 need not be incorporated into or with absorbent composite 62.

Still referring to FIG. 5, layer 64 can be liquid permeable or liquid impermeable, but desirably is liquid impermeable. More desirably, layer 64 is a multi-layer laminate in which the innermost layer 106 (FIG. 10) is liquid impermeable and the outermost layer 108 (FIG. 10) is liquid permeable. The innermost liquid impermeable layer 106 can be a 0.6 mil polyethylene film from Edison Plastics Company, and the outermost liquid permeable layer 108 can be a spunbond bicomponent polyethylene/polypropylene nonwoven web made of fibers from CHISSO Corporation. The outermost layer 108 may be C-folded over impermeable layer 106, as illustrated in FIG. 10.

Figure 6:
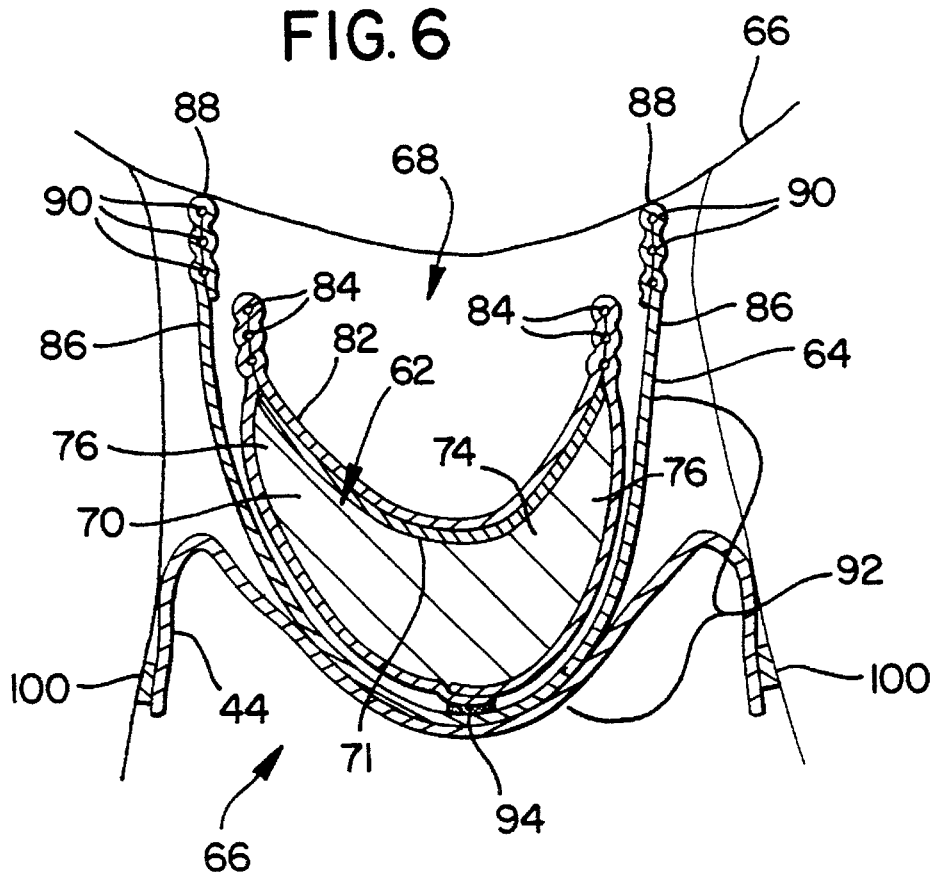
FIG. 6 is similar to FIG. 5 illustrating the effect of an urination.

Layer 64 includes a pair of side flaps 86 that have respective flap distal edges 88 that can extend laterally or transversely beyond corresponding absorbent side portions 76. Each flap distal edge 88 has a flap elastic member 90 elastically associated therewith. Flap elastic members 90 can be made of the same or different materials as absorbent elastic members 84. Layer 64 is laterally continuous in that it extends below or underneath absorbent composite 62 (FIG. 5) and laterally or transversely there beyond, so as to form side flaps 86 and flap distal edges 88. There also is an extendable area 92 that forms part of each side flap 86. This permits side flaps 86 to extend, as illustrated in FIGS. 5 and 6. Extendable areas 92 can be prefabricated in each side flap 86 in any suitable manner, such as by pleating, wrinkling, folding, or the like. Alternatively, layer 64 can be provided without any such prefabrication, and in this case will have a width, i.e., transverse measurement, of sufficient dimension that will result in the forming of extendable areas 92 during the initial fitting of the training pant at the crotch. In other words, when the distal edges 88 contact the crotch and the training pant is pulled further upwardly into the crotch, side flaps 86 will become compressed and shorten in length, thereby forming extendable areas, such as extendable areas 92. Furthermore, if desired, layer 64 or portions thereof can be made of any suitable elastic material, similar to those materials of which backsheet 44 can be made, that dispenses with the need to pleat, fold, or the like, since the elastic material will be inherently extendable.

Layer 64 is attached or joined to absorbent composite 62 by means of attachment area 94, which can be a single line, multiple lines, or single or multiple swirls of adhesive. Attachment area 94 can also be provided by numerous types of bonding, such as ultrasonic, heat, or the like. It is not necessary that the entire mutually facing surfaces between absorbent central portion 74 and layer 64 be totally adhered together. However, if the mutually facing surfaces are entirely adhered or attached, then extendable areas 92 should be carefully provided with the desired extension that at least equals or exceeds the sag or drop of a loaded absorbent composite 62. As illustrated in FIG. 5, a single narrow bead of adhesive at the crotch can suffice.

Referring now to FIG. 6, absorbent composite 62 is illustrated in a "loaded" condition, i.e., it has absorbed liquid waste, and under the weight of that absorbed liquid has sagged or moved downwardly from crotch 66. Important to the present invention is the fact that even though absorbent composite 62 has separated in distance from crotch 66 of the wearer, flap distal edges 88 have maintained contact with crotch 66 because of the extension of extendable areas 92 and the elastic influence of flap elastic members 90. One way of describing the mechanism of this seal or contact of distal edges 88 against crotch 66 is to refer to side flaps 86 as having dynamic flap heights, and absorbent side portions 76 as having static absorbent heights, in which the dynamic flap heights are greater than the static absorbent heights. The words "dynamic" and "static" in this description are better understood with reference to FIG. 6 which illustrates extendable areas 92 in a fully extended state with flap distal edges 88 still in contact with crotch 66, but with absorbent composite 62 separated in distance from crotch 66. The "dynamic" heights of side flaps 86 mean that the side flaps 86 extend and maintain contact with crotch 66 when absorbent composite 62 is loaded, and the "static" heights of absorbent side portions 76 mean that portions 76 do not maintain contact with crotch 66 when absorbent composite 62 is loaded. The weight of a loaded absorbent composite 62 will dictate whether and how much composite 62 separates from crotch 66. Dynamic flap heights and static absorbent heights generally will be in a range between about 25 to about 75 millimeters, with a dynamic flap height greater than a static absorbent height.

Figure 4:
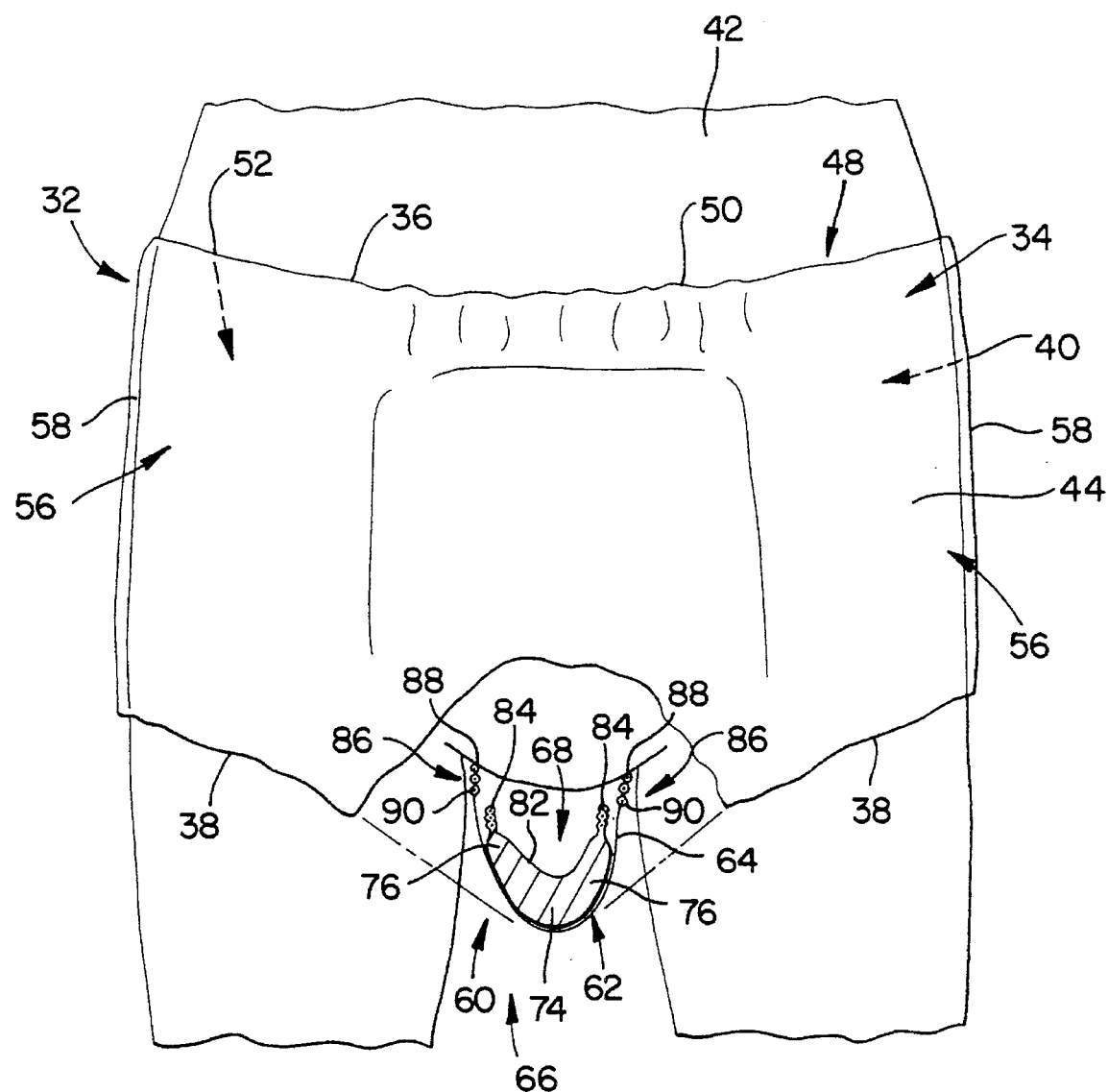
FIG. 4 is similar to FIG. 3 illustrating the effect on the crotch portion of the training pant after the wearer has urinated.

FIG. 3 illustrates absorbent composite 62 in an unloaded state, and flap distal edges 88, as well as absorbent side portions 76, being in contact with the body of the wearer. FIG. 4 illustrates absorbent composite 62 in a loaded state in which absorbent composite 62 has separated away from contact with the body of the wearer, but in which flap distal edges 88 continue to make sealing contact with the body, thereby improving containment of waste material.

FIG. 2 illustrates a differently designed or configured absorbent composite 62 in which there is a single weakened area 80 that permits composite 62 to assume a V-like shape. In this form of the invention, there is no absorbent central portion 74 between the absorbent side portions 76.

Figure 7:
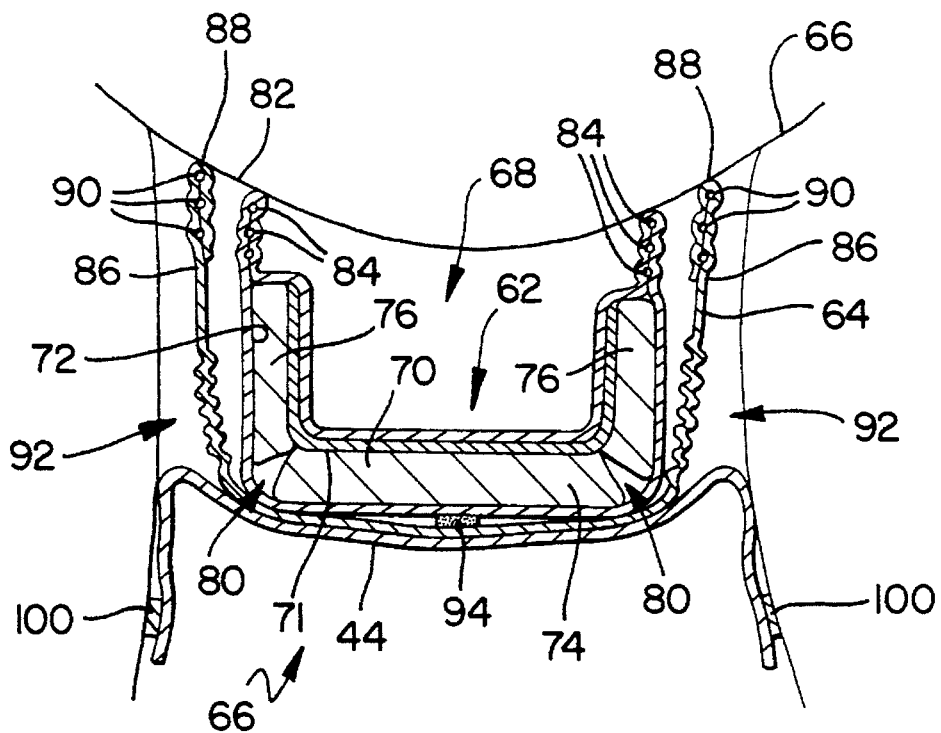
FIG. 7 illustrates a front elevational view in cross section of still another form of the present invention in the crotch of a wearer.
Figure 8:
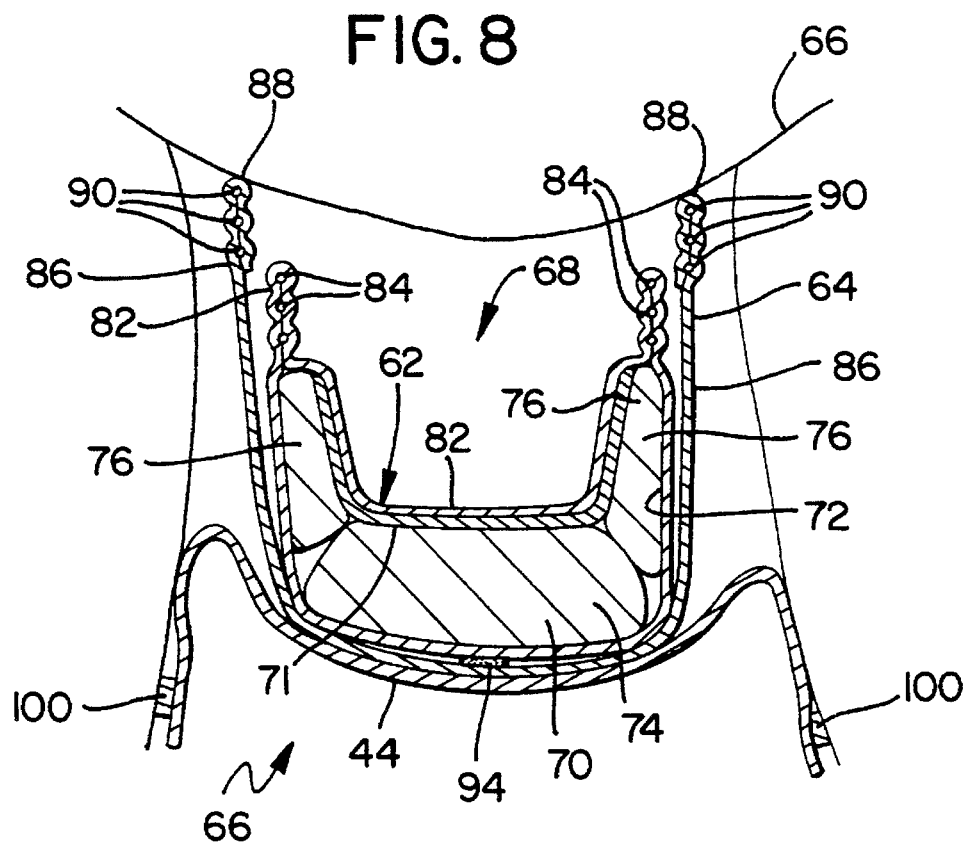
FIG. 8 is similar to FIG. 7 illustrating the effect after an urination.

FIGS. 7 and 8 illustrate another absorbent composite 62 that has a fluff/SAM mixture 70 that is relatively uniform in thickness. A pair of weakened areas 80 permit absorbent side portions 76 to move upwardly relative to absorbent central portion 74. Both flap distal edges 88 and absorbent side portions 76 are in contact with crotch 66. FIG. 8 illustrates absorbent composite 62 of FIG. 7 in a loaded state in which absorbent side portions 76 have separated from crotch 66, but in which flap distal edges 88 still maintain contact with crotch 66.

FIGS. 9–10 illustrate the construction of one form of the present invention. Specifically, with reference to FIG. 9, backsheet 44 is generally I-shaped with four elastic areas 96 elastically associated with respective ears 98. Ears 98 are formed by leg cut-outs 97 in backsheet 44. Elastic areas 96 can be formed of multiple strands of elastic material arranged in any fashion, such as parallel, intersecting, or both. Furthermore, elastic areas 96 can be a film or laminate of elastomeric material. Various materials and examples of providing elasticity at ears 98 are described in U.S. Pat. No. 4,940,464 and U.S. patent application Ser. No. 08/043,132 filed Mar. 25, 1993, both of which are incorporated by reference herein. These two incorporated references also disclose materials and methods of incorporating leg elastic members 100 in respective leg openings 38 (FIG. 3), and waist elastics 102 in respective front and back waist sections 48, 52. Also, backsheet 44 can be made of a single layer of elastic material, or a layer of elastic material with other non-elastic layers, as described earlier with reference to a SBL.

Continuing to refer to FIGS. 9 and 10, waist elastics 102 are adhesively attached to backsheet 44 by waist elastic adhesive 104. This adhesive and those following can be any suitable adhesive and applied in any suitable pattern. Suitable adhesives can be obtained from Findley Adhesives, Inc., Wauwatosa, Wis. The adhesives can be applied in any manner such as spraying, slot-coating extrusion, printing, or the like. The adhesive can be sprayed in any desired configuration or design such as continuous or discontinuous bead(s), discontinuous or continuous swirl(s), melt-blown pattern, spray pattern, or the like. Layer 64 is adhesively adhered to backsheet 44 by attachment adhesive 112. Attachment adhesive 112 should be applied with the same care and attention as attachment area 94 with regard to extendable areas 92. FIG. 10 further illustrates layer 64 as including liquid impermeable film 106 and a liquid permeable layer 108. The ends of permeable layer 108 are C-folded around film 106 and flap elastic members 90. Film 106 and permeable layer 108 are adhered together by laminating adhesive 110. Attachment area 94 adhesively attaches permeable layer 82 to layer 64, such as with parallel beads of adhesive, and is applied in an I-shaped pattern in which the laterally disposed portion of adhesive attaches the ends of layer 82 to layer 64. Permeable layer 82 is wrapped about absorbent composite 62 and adhesively secured thereto by adhesive spray 114. Flap adhesive 116 attaches the ends of side flaps 86 on top of absorbent side portions 76; the intermediate portions of side flaps 86 being unattached. Surge layer 71 is adhered to absorbent composite 62 by surge adhesive 118. Elastic areas 96 and leg elastic members 100 are adhered to backsheet 44 by area adhesive 120. Elastic areas 96 can also be provided in or to backsheet 44 as described earlier. The present invention also contemplates that the attachment of elements or structures can be accomplished other than by adhesives, such as by ultrasonic bonding, heat bonding, and the like.

In manufacturing one form of the present invention, backsheet 44 is supplied with leg cut-outs 97 in a continuously moving fashion and has leg elastic members 100 and waist elastics 102 applied in any suitable manner; one such manner is described in the aforementioned U.S. Pat. No. 4,940,464. Elastic areas 96 are applied or provided at respective ears 98; one such manner is describe in the aforementioned U.S. patent application Ser. No. 08/043,132. Absorbent composite 62 is positioned on the continuously moving backsheet 44. Absorbent composite 62 can be applied in a continuous manner or as separate, discrete absorbent structures. Absorbent composite 62 has weakened areas 80 provided therein, and this can occur either prior to or after absorbent composite 62 has been positioned on backsheet 44. Layer 64 is also provided in a continuous manner between absorbent composite 62 and backsheet 44. Backsheet 44 is separated, i.e., cut, transversely to form individual absorbent articles. Thereafter, ears 98 are joined together along their corresponding side edges 58 to form training pant 32. The adhering or bonding of these elements can be performed as describe above.

While this invention has been described as having a preferred embodiment, it will be understood that it is capable of further modifications. This application is therefore intended to cover any variations, equivalents, uses, or adaptations of the invention following the general principles thereof, and including such departures from the present disclosure as come or may come within known or customary practice in the art to which this invention pertains and falls within the limits of the appended claims.

What is claimed is:

1. A disposable absorbent child's training pant, comprising:
    a generally liquid permeable pant body comprising a front waist section, a back waist section, a crotch section, a waist opening, and a pair of leg openings,
    an absorbent composite disposed in said pant body at least at said crotch section thereof, said absorbent composite comprising a longitudinally extending absorbent central portion and a pair of longitudinally extending absorbent side portions, said absorbent central portion having a higher basis weight than one of said absorbent side portions, each said side portion having a static absorbent height,
    an elastic member elastically associated with each said absorbent side portion,
    a weakened area between each said absorbent side portion and said absorbent central portion for allowing each said absorbent side portion to be movable upwardly relative to said absorbent central portion,
    a liquid impermeable layer disposed between said absorbent composite and said pant body, said liquid impermeable layer being attached to said absorbent central portion and comprising a pair of longitudinally extending side flaps having respective flap distal edges and dynamic flap heights, said dynamic flap heights being greater than said static absorbent heights, and
    a flap elastic member elastically associated with each said flap distal edge for gathering a respective said side flap.

2. The pant of claim 1 wherein said absorbent central portion has a lower density than one of said absorbent side portions.

3. The pant of claim 1 further comprising a surge layer disposed with said absorbent composite.

4. The pant of claim 1 wherein said liquid impermeable layer is elastic.

5. The pant of claim 1 wherein said pant body is elastic.

6. A disposable absorbent pant, comprising:
    a liquid impermeable pant body comprising an interior space, a waist opening, a pair of leg openings, and a crotch section,
    an absorbent composite disposed in said interior space at said crotch section, said absorbent composite comprising an absorbent central portion and a pair of absorbent side portions,
    a weakened area between each said absorbent side portion and said absorbent central portion,
    a layer disposed between said absorbent composite and said pant body, said layer comprising a pair of side flaps having respective distal edges extending laterally beyond said absorbent side portions, and
    a flap elastic member elastically associated with each said flap distal edge for gathering a respective said side flap.

7. The pant of claim 6 wherein said layer is liquid permeable.

8. The pant of claim 6 wherein said layer is liquid impermeable.

9. The pant of claim 6 wherein each said absorbent side portion has a static absorbent height, and wherein each said side flap has a dynamic flap height, said dynamic flap height being greater than said static absorbent height.

10. The pant of claim 6 further comprising an elastic member elastically associated with each said absorbent side portion.

11. The pant of claim 6 further comprising a surge layer disposed on said absorbent composite.

12. The pant of claim 6 wherein said layer is elastic.

13. A disposable absorbent article, comprising:

a backsheet, an absorbent composite disposed on said liquid impermeable backsheet and comprising a longitudinally extending absorbent central portion and a pair of longitudinally extending absorbent side portions, a weakened area longitudinally extending between each said absorbent side portions and said longitudinally extending absorbent central portion, said absorbent central portion having a higher basis weight than one of said absorbent side portions, each said absorbent side portion having a static absorbent height, an elastic member being elastically associated with each said absorbent side portion.

a lliquid impermeable layer disposed between said absorbent composite and said backsheet, said liquid impermeable layer being attached to said absorbent central portion and comprising a pair of longitudinally extending side flaps having respective dynamic flap heights and flap distal edges that extend laterally beyond said absorbent side portions, said dynamic flap heights being greater than said static absorbent heights, and a flap elastic member elastically associated with each said flap distal edge for gathering a respective said side flap.

14. The article of claim 13 wherein said backsheet comprises a front waist section, a back waist section, a crotch section between said front section and said back section, and a pair of side sections, and forms a waist opening and a pair of leg openings.

15. The article of claim 13 wherein said backsheet is liquid permeable.

16. The article of claim 13 wherein said backsheet is liquid impermeable.

17. The article of claim 13 wherein said backsheet is elastic.

18. The article of claim 13 wherein said layer is elastic.

19. The article of claim 13 further comprising a surge layer disposed on said absorbent composite.

* * * * *